United States Patent
Lavelle et al.

(10) Patent No.: US 8,838,208 B2
(45) Date of Patent: Sep. 16, 2014

(54) FIDUCIAL DEPLOYMENT NEEDLE SYSTEM

(75) Inventors: Shay Lavelle, Co. Limerick (IE); Paul Devereux, Dublin (IE); Michael Clancy, Monaleen (IE)

(73) Assignee: Cook Medical Technologies LLC, Bloomington, IN (US)

(*) Notice: Subject to any disclaimer, the term of this patent is extended or adjusted under 35 U.S.C. 154(b) by 28 days.

(21) Appl. No.: 13/526,008

(22) Filed: Jun. 18, 2012

(65) Prior Publication Data

US 2013/0006286 A1    Jan. 3, 2013

Related U.S. Application Data

(60) Provisional application No. 61/502,063, filed on Jun. 28, 2011.

(51) Int. Cl.
- *A61B 6/00* (2006.01)
- *A61M 37/00* (2006.01)
- *A61B 17/34* (2006.01)
- *A61N 5/10* (2006.01)
- *A61B 19/00* (2006.01)

(52) U.S. Cl.
CPC ........ *A61M 37/0069* (2013.01); *A61B 17/3468* (2013.01); *A61B 2019/5495* (2013.01); *A61N 5/1049* (2013.01); *A61B 2019/5425* (2013.01); *A61B 2019/5466* (2013.01); *A61B 2019/5487* (2013.01); *A61B 19/54* (2013.01)
USPC ......................................................... 600/431

(58) Field of Classification Search
USPC ......................................................... 600/431
See application file for complete search history.

(56) References Cited

U.S. PATENT DOCUMENTS

| | | | |
|---|---|---|---|
| 2,009,393 | A | 7/1935 | Failla |
| 3,470,834 | A | 10/1969 | Bone |
| 3,815,798 | A | 6/1974 | Lavitch et al. |
| 4,700,692 | A | 10/1987 | Baumgartner |
| 4,716,901 | A | 1/1988 | Jackson et al. |
| 5,281,197 | A | 1/1994 | Arias et al. |
| 5,669,543 | A | 9/1997 | Ueno |
| 6,004,320 | A | 12/1999 | Casscells et al. |
| 6,210,315 | B1 | 4/2001 | Andrews et al. |

(Continued)

FOREIGN PATENT DOCUMENTS

| | | |
|---|---|---|
| EP | 0093101 A2 | 11/1983 |
| FR | 2 762 517 A1 | 4/1997 |
| JP | 6323312 A | 11/1994 |

OTHER PUBLICATIONS

Office Action for U.S. Appl. No. 12/764,432, mailing date May 9, 2012.

(Continued)

*Primary Examiner* — Jonathan Cwern
*Assistant Examiner* — Amelie R Gillman
(74) *Attorney, Agent, or Firm* — Brinks Gilson & Lione

(57) ABSTRACT

Embodiments include a fiducial deployment system. A fiducial may include dimples to enhance echogenicity and/or to provide for engagement with a delivery cannula or stylet. The needle system may be configured to deliver a plurality of fiducials to a target location in serial fashion, one at a time, when the fiducials are coaxially disposed around a central deployment member that may be embodied as a delivery cannula or stylet. In certain embodiments, echogenic placement of fiducials may present certain advantages. An elongate structure may be included that is configured to distally advance fiducials along the deployment member.

17 Claims, 3 Drawing Sheets

(56) References Cited

U.S. PATENT DOCUMENTS

| | | |
|---|---|---|
| 6,283,948 B1 | 9/2001 | McKernan et al. |
| 6,402,677 B1 | 6/2002 | Jacobs |
| 6,450,938 B1 | 9/2002 | Miller |
| 6,569,077 B2 | 5/2003 | Schmidt |
| 7,144,386 B2 | 12/2006 | Korkor et al. |
| 7,361,135 B2 | 4/2008 | Drobnik et al. |
| 7,615,076 B2 | 11/2009 | Cauthen, III et al. |
| 2003/0120141 A1 | 6/2003 | Adler |
| 2003/0233101 A1 | 12/2003 | Lubock et al. |
| 2003/0233126 A1 | 12/2003 | Kaplan et al. |
| 2007/0093726 A1* | 4/2007 | Leopold et al. ............... 600/562 |
| 2008/0287782 A1 | 11/2008 | Traboulsi et al. |
| 2009/0105584 A1 | 4/2009 | Jones |
| 2009/0227893 A1* | 9/2009 | Coonahan et al. ............ 600/566 |
| 2010/0137891 A1 | 6/2010 | Shalon et al. |
| 2010/0280367 A1* | 11/2010 | Ducharme et al. ............ 600/426 |
| 2011/0288581 A1* | 11/2011 | Paul et al. ..................... 606/213 |

OTHER PUBLICATIONS

Marker Kit, "Gold fiducial markers—Accurate localization for soft tissue targets," Best Medical International, Inc., Springfield, VA, Jan. 2008, pp. 43-54.

PCT Notification of Transmittal of the International Search Report and the Written Opinion of the International Searching Authority, or the Declaration for PCT Application No. PCT/US2010/031842, date of mailing Nov. 3, 2010.

* cited by examiner

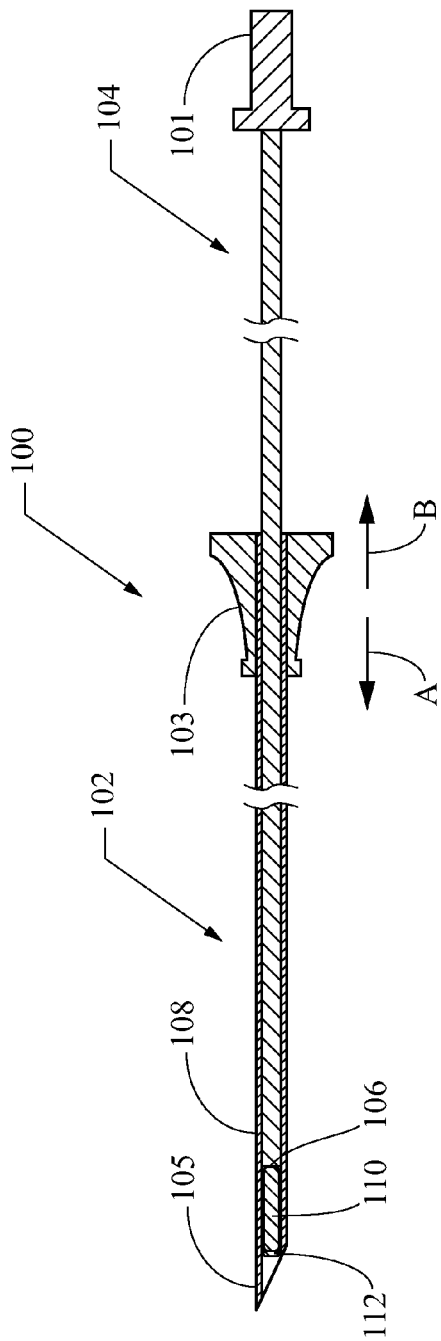
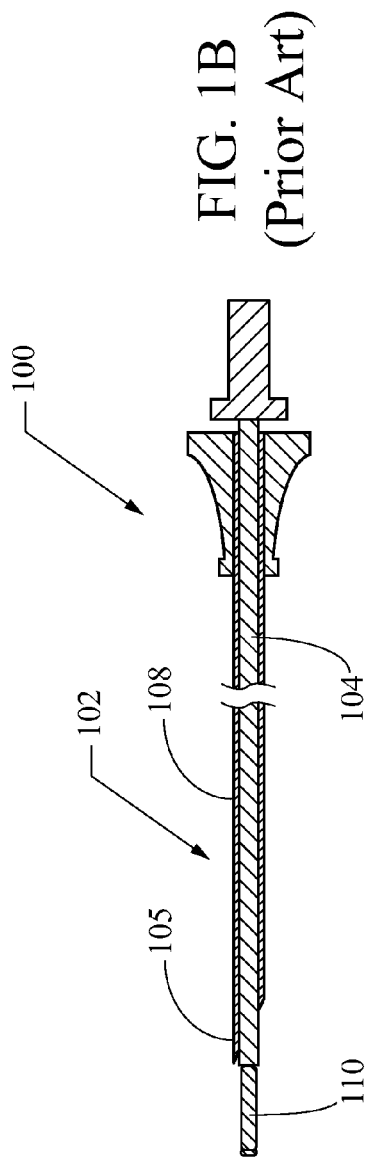

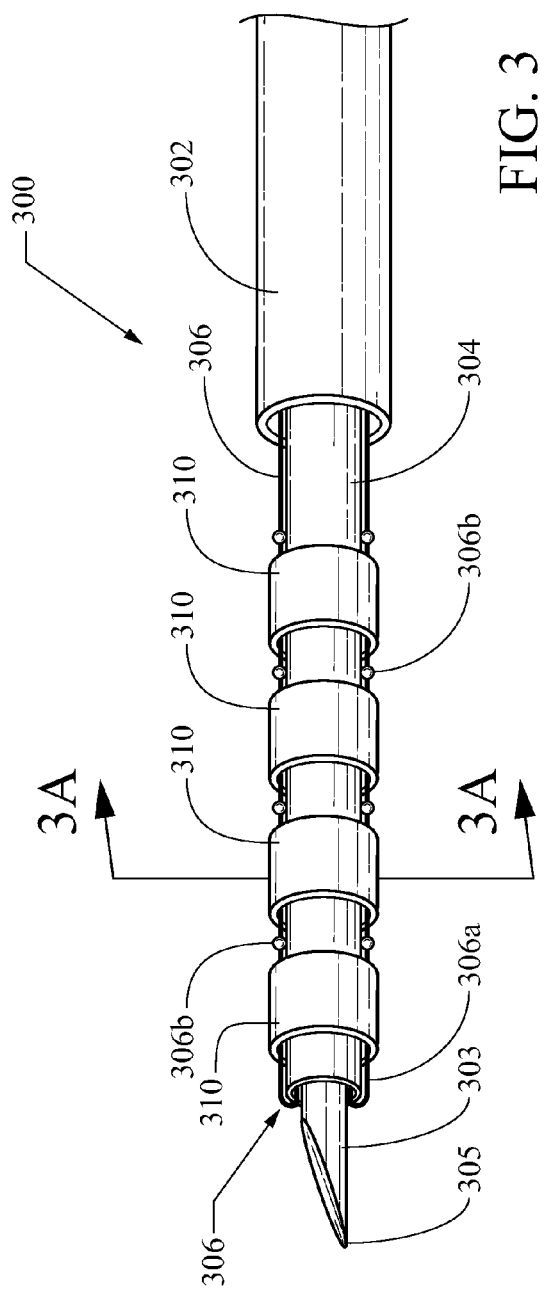
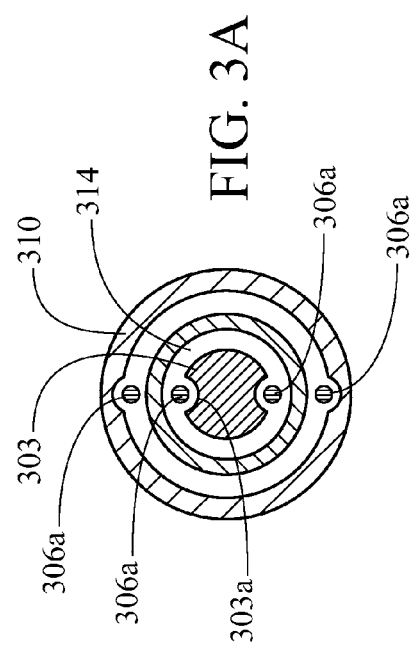

FIDUCIAL DEPLOYMENT NEEDLE SYSTEM

CROSS-REFERENCE TO RELATED APPLICATIONS

This application claims priority to U.S. Provisional Application Ser. No. 61/502,063, filed Jun. 28, 2011, which is incorporated herein by reference in its entirety.

TECHNICAL FIELD

The invention relates generally to a medical device system including one or more fiducials and methods of use for same. More particularly, the invention pertains to specially-configured fiducials, needles configured for use with them, and methods of use for same.

BACKGROUND

Medical procedures often require locating and treating target areas within a patient. Focused, dose-delivery radiation therapy—such as is applied during external beam radiation treatment—requires locating the target with a high degree of precision to limit damaging healthy tissue around the target. It is particularly important to know or estimate the precise location of the target in radiation oncology because it is desirable to limit the exposure of adjacent body parts to the radiation in a patient already suffering the depredations of cancer. However, in all treatment procedures, whether radiologic or otherwise, it is most desirable to be able to accurately target a region to be treated.

In many applications, it is not possible to directly view a treatment target or portion thereof (such as, for example, a cancerous tumor, cyst, pseudocyst, or other target) that needs to be acted on in some manner. As one example, when treating a lung or pancreatic tumor with radiation, it may not possible to view the actual tumor within the patient immediately before the radiation treatment. It is therefore highly advantageous to have some mechanism for permitting the tumor to be located accurately so that the radiation treatment can be targeted at the tumor while avoiding damage to healthy tissue.

Even for target regions that may be visualized using CAT (computer-assisted tomography) scans, MRI (magnetic resonance imaging), x-rays, ultrasound, or other techniques, difficulties often arise in targeting a treatment. This is particularly true for target regions within a torso of a patient and soft tissue regions. Due to the mobility of tissues in those regions (e.g., movement of internal organs during respiration and/or digestion, the movement of breast tissue with any change of body position), a target region may not remain fixed relative to anatomical landmarks and/or to marks that can be placed onto an external surface of a patient's body during one of those visualization procedures.

Several techniques have been developed to address this problem. One such technique is to place markers into the patient along the margins of the target region. The markers may be active (e.g., emitting some kind of signal useful in targeting a therapy) or passive (e.g., non-ferromagnetic gold markers—called fiducials—that can be used for targeting under ultrasound, MRI, x-ray, or other targeting techniques, which may be included in a treatment device).

A fiducial is typically formed of a radio-opaque material that the target can be effectively located and treated with a device that targets a site using the fiducials as positional markers under radiographic detection. Typically, the fiducials may be inserted into the patient during a simple operation. Percutaneous placement is most commonly used. However, use of minimally-invasive placement via an endoscope has recently developed for fiducial placement into a patient's internal organs. For example, percutaneous placement of fiducials along the margins of a pancreatic tumor can be complex and painful (particularly for obese patients, where the needle size is necessarily larger). Another process using percutaneously implanted objects in a patient is brachytherapy. In brachytherapy, radioactive sources or "seeds" are implanted into and/or adjacent a tumor to provide a high dose of radiation to the tumor, but not the healthy tissue surrounding the tumor.

FIGS. 1A and 1B show longitudinal sectional views of a two-piece introducer 100 of the prior art useful for placement of brachytherapy seeds or fiducials. Referring first to FIG. 1A, the introducer 100 includes a needle 102 and a stylet 104 slidably disposed within the needle 102. The stylet 104 includes a first handle 101 and a blunt distal end 106. The needle 102 includes a second handle 103 and a bevel-tipped cannula 108 extending through the second handle 103. The cannula 108 is configured to hold a seed/fiducial 110. The cannula 108 has a distal tip 105 configured for percutaneous implantation of the seed/fiducial 110 into the patient.

In a "pre-loaded configuration," the seed/fiducial 110 is retained in the cannula 108 by a plug 112 made from bone wax or other suitable bio-compatible material(s). This is typically accomplished by a "muzzle-loading" technique where the fiducial is placed into the distal needle and then held in place by the bone wax plug. This can present some challenges, as the bone wax plug 112 can be visible as an artifact in the patient, potentially interfering with clear visualization of body structures or treatment devices. With this configuration, the cannula 108 must be withdrawn and reloaded after delivery of each seed/fiducial 110. If the target locations for the fiducials are very far apart, use of a single percutaneous introducer cannula/trocar for multiple introductions of the cannula 108 may not be possible. In such a circumstance, the patient must endure several percutaneous punctures (and the increased attendant risk of infection for each).

To implant the desired arrangement of seeds/fiducials 110 at a target location in a patient, an operator pushes the cannula 108 in a first direction (arrow A) to insert the tip 105 into the patient (typically under fluoroscopic visualization). The operator then pushes the second handle 103 further in the first direction to position the tip 105 at the desired depth within the patient where a seed/fiducial 110 is to be implanted. Throughout this motion, the operator moves the needle 102 and the stylet 104 together as a unit. At the desired depth/location, the operator grasps the first handle 101 with one hand and the second handle 103 with the other hand. Then, the operator holds the first handle 101 stationary while simultaneously sliding the second handle 103 back in a second direction (arrow B) toward the first handle 101. As shown in FIG. 1B, this movement causes the cannula 108 to retract over the seed/fiducial 110 to implant it in the patient. Alternatively, the operator may move the first handle 101 in the first direction (arrow A) while sliding the second handle 103 back in the second direction (arrow B). This causes the stylet 104 to push the seeds 110 out of the cannula 108. The procedure is then repeated to place other seeds/fiducials 110. When being used for targeting of radiation therapy, a minimum of three fiducials is typically required.

As will be appreciated from the disclosed structure, after deploying one fiducial, one may alternatively reload the introducer 100 from the proximal end by completely withdrawing the stylet 104, then placing another fiducial into the needle lumen and advancing it therethrough to a second location to which the distal needle tip 105 has been directed (a "breech-loading" technique). Provided that the fiducial target sites are sufficiently close together to allow this technique, it can reduce the number of percutaneous punctures or other access procedures needed to place more than one fiducial. However, it creates a problem for procedures where ultrasound is being used or is to be used in the near-future because it introduces air pockets into the tissue and related fluids. Those air pockets with tissue and/or fluid are echogenic in a manner that can interfere with ultrasound visualization of a target area and/or tools being used to diagnose or treat in/around the area. In some brachytherapy techniques, a series of fiducials may be preloaded into the needle—either separately or connected by a suture or similar device—then placed together in fairly close proximity; however, such a technique typically is not effective for placing three or more fiducials in sufficiently disparate locations to use for targeting a treatment relative to, for example, margins of a tumor.

The process is similar when implemented endoscopically in the manner developed rather recently, except that the needle and stylet are of the type known in the art for use through the working channel of an endoscope. One limitation of current endoscopic techniques is the size of fiducial that can be introduced. With the size limitation of endoscope working channels, the largest needle that can typically be used without risking bending, crimping, curving or otherwise damaging a needle (that does not have an internal stylet or other support) during advancement out of the endoscope to an anatomical target is a 19-gauge needle. This limits the size of the fiducial that can be introduced through the needle lumen using current, cylindrical fiducials. The endoscopic technique generally suffers from the same reloading problems as described above. Even though the external percutaneous punctures are not an issue, having to withdraw and reload takes up valuable time and complicates the procedure, potentially requiring additional personnel, whether only the stylet is withdrawn for "breech-loading" or the entire device is withdrawn for "muzzle-loading."

It would be desirable to provide multiple fiducials in a needle that can be introduced in a controlled serial manner (one at a time) rather than requiring manual reloading after placement of each fiducial.

BRIEF SUMMARY

Embodiments of a fiducial deployment needle system described herein may include a plurality of fiducials having a central aperture and configured to be delivered over a stylet. The fiducials may be dimpled or otherwise configured in a manner to promote engagement with and retention upon the stylet until a desired deployment time and location. The fiducial needle system may be configured to deploy the fiducials by advancement of a sheath or a beaded wire. The embodiments generally will include a needle configured for delivering a plurality of fiducials in serial fashion, and a method of delivering one or more fiducials to a target region.

Embodiments may include a fiducial deployment system. A fiducial may include dimples to enhance echogenicity and/or to provide for engagement with a delivery cannula or stylet. The needle system may be configured to deliver a plurality of fiducials to a target location in serial fashion, one at a time, when the fiducials are coaxially disposed around a central deployment member that may be embodied as a delivery cannula or stylet. In certain embodiments, echogenic placement of fiducials may present certain advantages. An elongate structure may be included that is configured to distally advance fiducials along the deployment member.

BRIEF DESCRIPTION OF THE DRAWINGS

FIGS. 1A-1B show a prior art fiducial introducer and method of use;

FIG. 3 shows a second embodiment of a fiducial deployment needle system; and

FIG. 3A shows a transverse section view of the embodiment of FIG. 3A along line 3A-3A.

DETAILED DESCRIPTION

The terms "proximal" and "distal" are used herein in the common usage sense where they refer respectively to a handle/doctor-end of a device or related object and a tool/patient-end of a device or related object.

Figure 2:
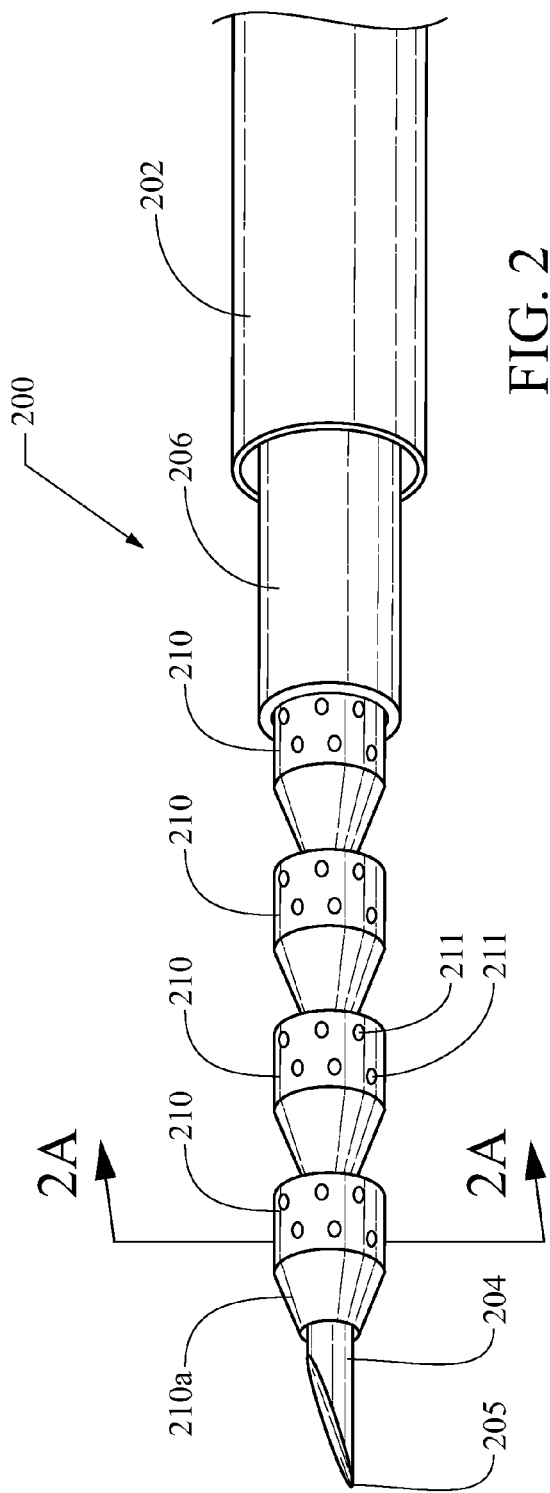
FIG. 2 shows a first embodiment of a fiducial deployment needle system.
Figure 2A:
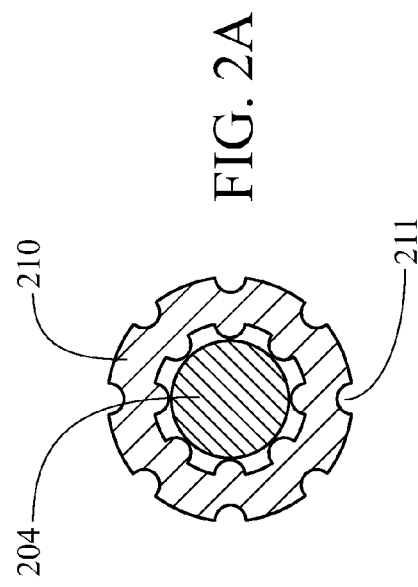
FIG. 2A shows a transverse section view of the embodiment of FIG. 2A along line 2A-2A.

A fiducial deployment needle system 200 is described with reference to FIGS. 2-2A. The system 200 includes an elongate outer sheath 202 that may be configured to protect the working lumen of an endoscope or other introduction means. The system 200 preferably is configured with a length, flexibility, and manipulability for use with a gastrointestinal endoscope, or other minimally invasive device configured for directing surgical tools to a target site within a patient body of a human or non-human patient. In some embodiments, the device may be configured for percutaneous use, wherein the outer sheath is configured as a penetrating needle or trocar constructed to provide access for the internal system components.

The outer sheath 202 includes a longitudinal lumen through which an elongate fiducial-carrying member embodied as a stylet 204 coaxially (and manipulably) extends. The stylet 204 is illustrated here as including a penetrating distal tip 205 that will facilitate its use in providing access to a target site for fiducial deployment. "Fiducial deployment" (or placement) refers to positioning of a fiducial in a target region (e.g., at a tumor margin). A plurality of fiducials 210 is disposed generally coaxially around a distal region of the stylet 204. A movable structure for fiducial deployment, embodied here as a pusher sheath 206 is also disposed slidably about the stylet 204, which extends through a longitudinal pusher sheath lumen. The pusher sheath 206 is configured for pushing the fiducials 210 distally along the length of the stylet. As such, its inner diameter preferably is the same or at least slightly greater than the outer diameter of the stylet, but less than the outer diameter of the fiducials (or at least of the proximal-most fiducial to be advanced).

Each of the fiducials 210 shown includes a tapered distal end region 210*a* configured to ease penetration of tissue during advancement of the stylet 204. Each of the fiducials 210 also includes one or more dimples 211. The dimples 211 may be multifunctional. For example, the dimples 211 may enhance echogenicity and/or fluoroscopic visualization of the fiducials 210, which preferably are constructed of or at least include a radio-opaque material. When the fiducials are disposed on the stylet 204, this effect may also enhance visualizability of the stylet, which may provide advantages for directing it to a target site. As shown in the transverse section view of FIG. 2A, the dimples 211 may also provide for a frictional engagement of the fiducials 210 with the stylet 204, as they may extend into the central aperture of the fiducial that rides coaxially along the stylet in a manner that grips the external stylet surface.

Frictional engagement of the fiducials 210 with the stylet 204 may prevent inadvertent deployment of the fiducials (e.g., prematurely and/or more than one at a time). The stylet 204 may include one or more concentric grooves and/or ridges (not shown) that may facilitate engagement with the fiducial dimples 211. Such concentric grooves and/or ridges may provide tactile feedback to a user when a fiducial 210 is advanced due to increased and decreased resistance during transition.

In a method of fiducial deployment, the system 200 may be directed to a target site. This may be done, for example, via a gastrointestinal endoscope, a percutaneous trocar, or other introduction means. Ocular, fluoroscopic, and/or ultrasound visualization may be used to navigate the distal end of the stylet 204 near to a target region. The outer sheath 202 may be used during navigation of the system through at least a working channel of an introducer device (e.g., trocar, endoscope working channel). When the system 200 is desirably positioned, the stylet 204 with its overlying fiducials may be advanced through tissue to a target site for a first fiducial.

When the distal stylet end and distal-most fiducial are in a first desired location, the pusher sheath 206 may be advanced, and/or the stylet 204 may be retracted to deploy the distalmost fiducial in the desired location. The stylet 204 may then be directed to a second desired location, and the same procedure repeated. These steps may be repeated to place a desired number of fiducials into target locations. For many forms of targeted external beam radiation, it may be desirable to place at least three or more fiducials at or near the margins of a tumor or other region that is to receive targeted treatment.

The fiducials described in different embodiments of the present application may be understood with reference to, and may be modified in a manner similar to that described in U.S. Pat. App. Pub. Nos. 2010/0280367 and 2011/0152611, each of which is incorporated herein by reference. Deployment mechanisms (e.g., such as may be used in a device handle) may also be understood with reference to these documents.

A fiducial deployment needle system 300 is described with reference to FIGS. 3 and 3A. The system 300 includes an elongate outer sheath 302 that may be configured to protect the working lumen of an endoscope or other introduction means, then retracted during actuation of the fiducial deployment elements. The system 300 preferably is configured with a length, flexibility, and manipulability for use with a gastrointestinal endoscope, or other minimally invasive device configured for directing surgical tools to a target site within a patient body of a human or non-human patient. In some embodiments, the device may be configured for percutaneous use, wherein the outer sheath is configured as a penetrating needle or trocar constructed to provide access for the internal system components.

The outer sheath 302 includes a longitudinal lumen through which an elongate fiducial-carrying member embodied as a delivery cannula 304 coaxially (and manipulably) extends. A stylet 303 is illustrated here as disposed through a delivery cannula lumen 314 and including a penetrating distal tip 305 that will facilitate its use in providing access to a target site for fiducial deployment. "Fiducial deployment" (or placement) refers to positioning of a fiducial in a target region (e.g., at a tumor margin). A plurality of fiducials 310 is disposed generally coaxially around a distal region of the delivery cannula 304 (in this and other embodiments the fiducials may be tubular, have a C-shaped cross section, or any other geometry that allows them to engage around an elongate fiducial-carrying deployment member). At least one movable structure for fiducial deployment, embodied here as a flexible elongate member 306 is disposed slidably along an external length of, then following back along an internal/lumenal length of, the delivery cannula 304. The flexible elongate member 306 is configured for pushing the fiducials 310 distally along the length of the delivery cannula.

The flexible elongate member 306 may include a central member 306a configured as a wire, polymer filament, or similar structure. At least one engagement structure 306b is disposed on the central member 306a. The at least one engagement structure 306b may include a widened portion of the central member 306a, a bead, or another structure that will engage with a fiducial 310 sufficiently to move it when the flexible elongate member 306 is actuated. A second, similar or identical flexible elongate member structure may be included as illustrated in FIGS. 3 and 3A. As will also be appreciated with reference to FIGS. 3 and 3A, the fiducials 310 may be advanced serially, one at a time, over the distal end of the delivery cannula 304 by actuation of the flexible elongate member 306 that includes distal movement of its portion that is external of the cannula and proximal movement of its portion that is in the cannula lumen. The engagement structure 306b proximally adjacent each fiducial 310 will advancingly press against it with this actuation, and will thereby advance the fiducial distally off the distal end of the delivery cannula 304.

As shown in the transverse section view of FIG. 3A, the fiducials 310 may include a frictional engagement around the cannula 304 and the flexible elongate member 306. In addition to the inherent retention ability of an engagement structure 306b distal of a given fiducial, such a frictional engagement may also help retain fiducials on the cannula until a desired deployment. FIG. 3A also shows that the stylet 303 may include grooves 303a configured to accommodate the proximal movement of engagement structures 306b within the delivery cannula lumen 314.

It will be appreciated from FIGS. 3 and 3A that advancement of an engagement structure 306b past and around the distal end of the cannula 304 (from traveling distally along its exterior to traveling proximally along its interior) may provide tactile feedback to a user as that action deploys a fiducial 310. This tactile feedback may assist a physician during deployment (which may also use ultrasound and/or fluoroscopic imaging). The fiducials 310 in this embodiment may be configured with dimples and/or a tapered configuration as in the embodiment of FIG. 2. They may also be configured in any other appropriate manner adaptable to the described deployment mechanism. Those of skill in the art will appreciate that a variety of handle mechanisms may be configured or adapted to effect the mechanical operation of the embodiments described herein.

In a method of fiducial deployment, the system 300 may be directed to a target site. This may be done, for example, via a gastrointestinal endoscope, a percutaneous trocar, or other introduction means. Ocular, fluoroscopic, and/or ultrasound visualization may be used to navigate the distal end of the cannula 304 near to a target region. The outer sheath 302 may be used during navigation of the system through at least a working channel of an introducer device (e.g., trocar, endoscope working channel). The stylet 303 may be used to penetrate through tissue to a first target location. When the system 300 is desirably positioned, the cannula 304 with its overlying fiducials 310 may be advanced through tissue to a target site for a first fiducial.

When the distal stylet end and distal-most fiducial are in a first desired location, the flexible elongate member 306 may be actuated such that its exterior portion is advanced so that the distalmost engagement structure 306b pushes and deploys the distalmost fiducial in the desired location. The distal end of the system may then be directed to a second desired location, and the same procedure repeated. These steps may be repeated to place a desired number of fiducials into target locations. For many forms of targeted external beam radiation, it may be desirable to place at least three or more fiducials at or near the margins of a tumor or other region that is to receive targeted treatment, which will preferably allow accurate triangulation for targeting of the treatment.

The fiducials described in different embodiments of the present application may be understood with reference to, and may be modified in a manner similar to that described in U.S. Pat. App. Pub. Nos. 2010/0280367 and 2011/0152611, each of which is incorporated herein by reference. Deployment mechanisms (e.g., such as may be used in a device handle) may also be understood with reference to these documents.

Fiducial embodiments may be formed of a radio-opaque, non-ferromagnetic material such as, for example, gold, platinum, palladium, iridium, or alloys thereof, with one preferred embodiment including an alloy of palladium with rhenium (advantages of which may include desirable radio-opacity, market-price stability superior to gold, and ultrasound-reflectivity/echogenicity due to density). Being radio-opaque will allow the fiducial to be used in deployment techniques using fluoroscopy, as well as making it detectible/visualizable by radiographic means during a treatment or other procedure where it may be desirable to know the location(s) of one or more fiducials. Being non-ferromagnetic will lessen the likelihood that visualization techniques or other procedures employing magnetic fields such as, for example, MRI, will re-orient or otherwise dislodge a fiducial. Echogenic construction of a fiducial or needle may be enhanced by surface texture, but can also be provided by structural inclusions such as embedded bubbles or beads that provide for a different ultrasound reflectivity than material surrounding them. Fiducials may also be coated with a material (e.g., parylene) configured to reduce backscatter during radiography.

The ability to complete fiducial deployment using direct/video and/or ultrasound imaging with little or no use of fluoroscopy may present an advantage of minimizing the cumulative radiation exposure of the patient (who may, for example, have to undergo radiation therapies where the total amount of exposure to radiation is desired to be minimized to that which is therapeutically and diagnostically necessary). Advantages of time and expense for the patient, physician and other treating/diagnostic personnel, and the treatment facility are likely as implementation of the present method may prevent all of those entities from having to schedule and conduct a second endoscopic procedure, and/or to extend the initial diagnostic procedure with the time-consuming methods and materials currently available in the prior art as described.

Drawings and particular features in the figures illustrating various embodiments are not necessarily to scale. Some drawings may have certain details magnified for emphasis, and any different numbers or proportions of parts should not be read as limiting, unless so-designated by one or more claims. Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. For example, a needle and fiducials of the present system may be used percutaneously, including in another minimally invasive surgical procedure, such as a laparoscopic-type procedure, within the scope of the claimed invention. For example, a target site may be a location in or near the gastrointestinal tract (e.g., liver, pancreas) such as those locations that may be accessible by endoscopy (using a minimally invasive endoscope introduced through a natural patient orifice, e.g., mouth, anus, vagina). This includes—more broadly—sites reachable through NOTES (natural orifice translumenal endoscopic surgery) procedures. The present method and device may also be used with other minimally-invasive surgical techniques such as percutaneous endoscopic procedures (e.g., laparoscopic procedures) or percutaneous non-endoscopic procedures, but most preferably is used with less invasive endoscopy procedures where the system embodiments are configured with a length and flexibility for navigation through a gastrointestinal endoscope to a target site. It is therefore intended that the foregoing detailed description be regarded as illustrative rather than limiting. And, it should be understood that the following claims, including all equivalents, are intended to define the spirit and scope of this invention.

We claim:

1. A fiducial deployment needle system comprising:
   an outer sheath having a longitudinal outer sheath lumen;
   an elongate fiducial-carrying member disposed coaxially through the outer sheath lumen;
   a plurality of fiducials disposed along a distal portion of the fiducial-carrying member, where each of the fiducials includes a central aperture engaged around the fiducial-carrying member; and
   a movable structure configured to advance the fiducials distally relative to the fiducial-carrying member;
   wherein the fiducial-carrying member is configured as a delivery cannula, and the movable structure is configured as a flexible elongate deployment member including a first length disposed along an external surface of the delivery cannula and a second length, continuous with the first length, extending around a distal end of the delivery cannula into the delivery cannula lumen,
   wherein the flexible elongate deployment member includes at least one engagement structure proximally located relative to at least one of the plurality of fiducials such that distal-ward advancement of the first length and proximal-ward movement of the second length will distally advance, in conveyor-like fashion, the at least one of the plurality of fiducials.

2. The system of claim 1, wherein the at least one engagement structure comprises a plurality of engagement structures distributed such that at least one engagement structure is proximally adjacent each of the plurality of fiducials.

3. The system of claim 1, wherein the flexible elongate deployment member comprises a wire and/or a polymer filament.

4. The system of claim 1, further comprising a second flexible elongate deployment member and at least one engagement structure proximally located relative to at least one of the plurality of fiducials.

5. The system of claim 1, wherein the at least one engagement structure comprises at least one bead fixed to the flexible elongate deployment member.

6. The system of claim 1, configured wherein a proximal advancement of the flexible elongate deployment member second length will move the at least one engagement structure distally a sufficient distance to advance distally past the distal end of the delivery cannula.

7. The system of claim 1, further comprising an outer sheath having a longitudinal outer sheath lumen through which the delivery cannula and stylet are coaxially disposed.

8. A fiducial deployment needle system comprising:
an elongate delivery cannula including a longitudinal lumen therethrough;
an elongate stylet disposed slidably through the delivery cannula lumen;
a plurality of fiducials disposed slidably on a distal portion of the delivery cannula, where each of the fiducials includes a central aperture engaging an external surface of the delivery cannula; and
a flexible elongate deployment member including a first length disposed along an external surface of the delivery cannula and a second length, continuous with the first length, extending around a distal end of the delivery cannula into the delivery cannula lumen, wherein the flexible elongate deployment member includes at least one engagement structure proximally located relative to at least one of the plurality of fiducials such that distal-ward advancement of the first length and proximal-ward movement of the second length will distally advance, in conveyor-like fashion, the at least one of the plurality of fiducials.

9. The system of claim 8, wherein the at least one engagement structure comprises a plurality of engagement structures distributed such that at least one engagement structure is proximally adjacent each of the plurality of fiducials.

10. The system of claim 8, wherein the flexible elongate deployment member comprises a wire and/or a polymer filament.

11. The system of claim 8, further comprising a second flexible elongate deployment member and at least one engagement structure proximally located relative to at least one of the plurality of fiducials.

12. The system of claim 8, wherein the at least one engagement structure comprises at least one bead fixed to the flexible elongate deployment member.

13. The system of claim 12, wherein the stylet comprises at least one longitudinal groove configured to allow proximal passage of a bead that has been advanced past and around the distal end of the delivery cannula.

14. The system of claim 8, configured wherein a proximal advancement of the flexible elongate deployment member second length will move the at least one engagement structure distally a sufficient distance to advance past the distal end of the delivery cannula.

15. The system of claim 8, further comprising an outer sheath having a longitudinal outer sheath lumen through which the delivery cannula and stylet are coaxially disposed.

16. A method of fiducial deployment comprising steps of:
providing a fiducial deployment needle system according to claim 1 and directing a distal portion of the fiducial-carrying member adjacent a target site;
directing the at least one engagement structure against one of the plurality of fiducials in a manner directing the fiducial past the distal end of the delivery cannula.

17. A method of fiducial deployment comprising steps of:
providing a fiducial deployment needle system according to claim 8 and directing a distal portion of the fiducial-carrying member adjacent a target site;
directing the at least one engagement structure against one of the plurality of fiducials in a manner directing the fiducial past the distal end of the delivery cannula.

* * * * *